US011705677B2

(12) United States Patent
Ritchie, Jr.

(10) Patent No.: US 11,705,677 B2
(45) Date of Patent: Jul. 18, 2023

(54) WATER-IN-FUEL SENSOR AND METHOD OF ASSEMBLY THEREOF

(71) Applicant: Group Dekko, Inc., Fort Wayne, IN (US)

(72) Inventor: James A. Ritchie, Jr., Fort Wayne, IN (US)

(73) Assignee: Group Dekko, Inc., Fort Wayne, IN (US)

(*) Notice: Subject to any disclaimer, the term of this patent is extended or adjusted under 35 U.S.C. 154(b) by 141 days.

(21) Appl. No.: 17/029,219

(22) Filed: Sep. 23, 2020

(65) Prior Publication Data
US 2022/0094118 A1 Mar. 24, 2022

(51) Int. Cl.
| H01R 13/66 | (2006.01) |
| G01N 33/28 | (2006.01) |
| H01R 103/00 | (2006.01) |
| H01R 43/02 | (2006.01) |

(52) U.S. Cl.
CPC ..... *H01R 13/6683* (2013.01); *G01N 33/2835* (2013.01); *G01N 33/2847* (2013.01); *H01R 43/0256* (2013.01); *H01R 2103/00* (2013.01)

(58) Field of Classification Search
CPC ............ H01R 13/6683; H01R 43/0256; G01N 33/2835; G01N 33/2847
USPC ...................................................... 73/61.43
See application file for complete search history.

(56) References Cited

U.S. PATENT DOCUMENTS

| 4,801,865 A * | 1/1989 | Miller ................. G01N 33/246 324/609 |
| 5,402,683 A * | 4/1995 | Kosugi ................... G01L 23/10 73/756 |
| 6,581,438 B1 * | 6/2003 | Hall ....................... G01N 13/02 73/53.01 |
| 7,581,965 B1 * | 9/2009 | Upasani .................. H05K 3/32 439/82 |
| 9,570,836 B2 * | 2/2017 | Nakanishi .............. H01R 43/18 |
| 10,707,598 B2 * | 7/2020 | Fu ......................... H01R 12/515 |
| 2007/0049121 A1 * | 3/2007 | Steele .................... H05K 5/064 439/630 |
| 2013/0031963 A1 | 2/2013 | Ritchie, Jr. et al. |

* cited by examiner

*Primary Examiner* — David Z Huang
*Assistant Examiner* — Jean F Morello
(74) *Attorney, Agent, or Firm* — Taylor IP, P.C.

(57) ABSTRACT

A method of assembling a water-in-fuel sensor assembly. The method includes an initial step of providing a housing that has a recess, at least one pin located within the housing, a circuit board, and at least one terminal configured for engaging the at least one pin. The method also includes forming a board-mounting subassembly by coupling the at least one terminal to the circuit board. The method also includes positioning the board-mounting subassembly within the housing by engaging the at least one terminal with the at least one pin such that the board-mounting subassembly is disposed within the recess of the housing.

20 Claims, 4 Drawing Sheets

WATER-IN-FUEL SENSOR AND METHOD OF ASSEMBLY THEREOF

BACKGROUND OF THE INVENTION

1. Field of the Invention

The present invention relates to engine systems, and, more particularly, to a water-in-fuel sensor assembly for an engine system.

2. Description of the Related Art

Some engine systems may include a fuel filtration system. Such a fuel filtration system may include a fuel filter canister, a fuel filter, and a water-in-fuel (WIF) sensor coupled to the engine control unit (ECU).

When the amount of the water in the fuel filter canister reaches a particular level, the water will contact the WIF sensor. The ECU will accordingly determine the amount of water present in the fuel by measuring a change in the voltage which is originally supplied to the WIF sensor. In more detail, the ECU measures the ratio from the supplied voltage to the analog sensor output of the WIF sensor. The ECU then converts the analog sensor output to a digital signal which the microcontroller can use in its calculations. If the detected change in voltage is within a predefined value which is indicative of an unacceptable amount of water in the fuel, the ECU can take remedial action to alert the operator by activating an indicator light, audible alarm, etc. Thereby, the operator may take the appropriate action to remove the water which is present in the fuel.

Generally, a WIF sensor includes a housing, one or more electrodes or pins for detecting a level of electrical resistance, and a circuit board that is electrically coupled to the one or more pins. The one or more pins extend into the interior of the fuel filter canister such that the water which is present in the fuel filter canister will contact the one or more pines upon reaching a particular level. Typically, the circuit board includes its own housing or overmold which is connected to the pins. The process of coupling the circuit board to the one or more pins may be cumbersome.

What is needed in the art is a cost-effective and easy-to-assemble WIF sensor.

SUMMARY OF THE INVENTION

The present invention provides a water-in-fuel (WIF) sensor assembly and a method for assembly thereof. The WIF sensor assembly generally includes a housing, at least one pin located within the housing, and a board-mounting subassembly located within the housing. The board-mounting subassembly includes a circuit board and at least one terminal coupled to the circuit board. The at least one terminal is engaged with the at least one pin such that the board-mounting subassembly is disposed within a recess of the housing.

The invention in one form is directed to a method of assembling a water-in-fuel sensor assembly. The method includes an initial step of providing a housing that has a recess, at least one pin located within the housing, a circuit board, and at least one terminal configured for engaging the at least one pin. The method also includes forming a board-mounting subassembly by coupling the at least one terminal to the circuit board. The method also includes positioning the board-mounting subassembly within the housing by engaging the at least one terminal with the at least one pin such that the board-mounting subassembly is disposed within the recess of the housing.

The invention in another form is directed to a WIF sensor assembly. The WIF sensor assembly includes a housing with a recess, at least one pin located within the housing, and a board-mounting subassembly located within the housing. The board-mounting subassembly includes a circuit board and at least one terminal coupled to the circuit board. The at least one terminal is engaged with the at least one pin such that the board-mounting subassembly is disposed within the recess of the housing.

An advantage of the present invention is that the board-mounting subassembly jointly combines the circuit board, one or more terminals, and one or more resistors into a collective body which is easily installed or removed from the housing of the WIF sensor assembly.

Another advantage of the present invention is that the one or more terminals easily mounts the circuit board onto the one or more pins of the WIF sensor assembly.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
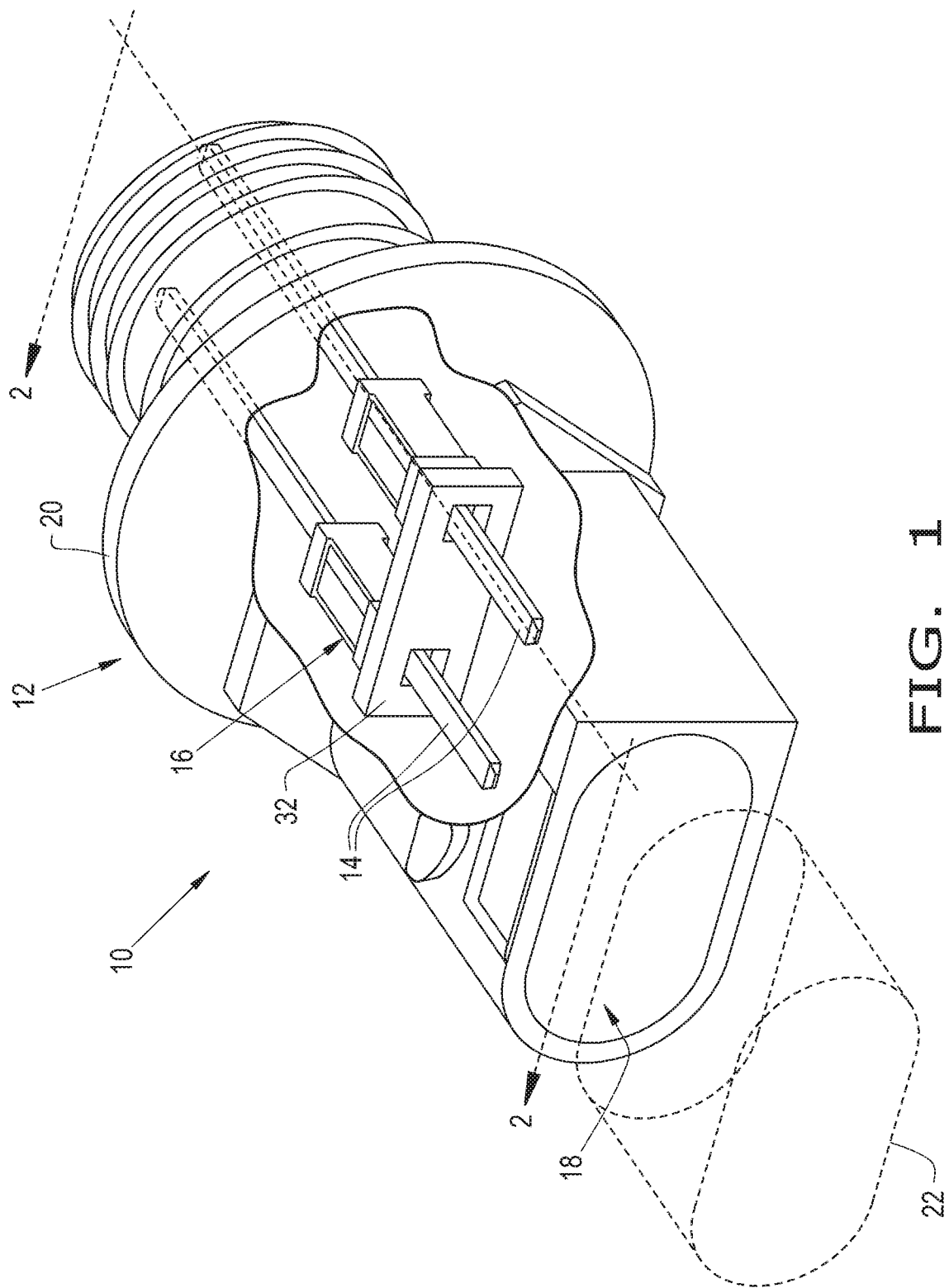
FIG. 1 is a perspective and partial cutaway view of an embodiment of a water-in-fuel sensor assembly.

Referring now to the drawings, and more particularly to FIGS. 1-4, there is shown a water-in-fuel (WIF) sensor assembly 10. The WIF sensor assembly 10 may be used in an engine system for measuring an amount of water which may be present in the fuel. The WIF sensor assembly 10 may generally include a housing 12, one or more pins or probes 14 located within the housing 12, and a board-mounting subassembly 16 located within the housing 12.

Figure 2:
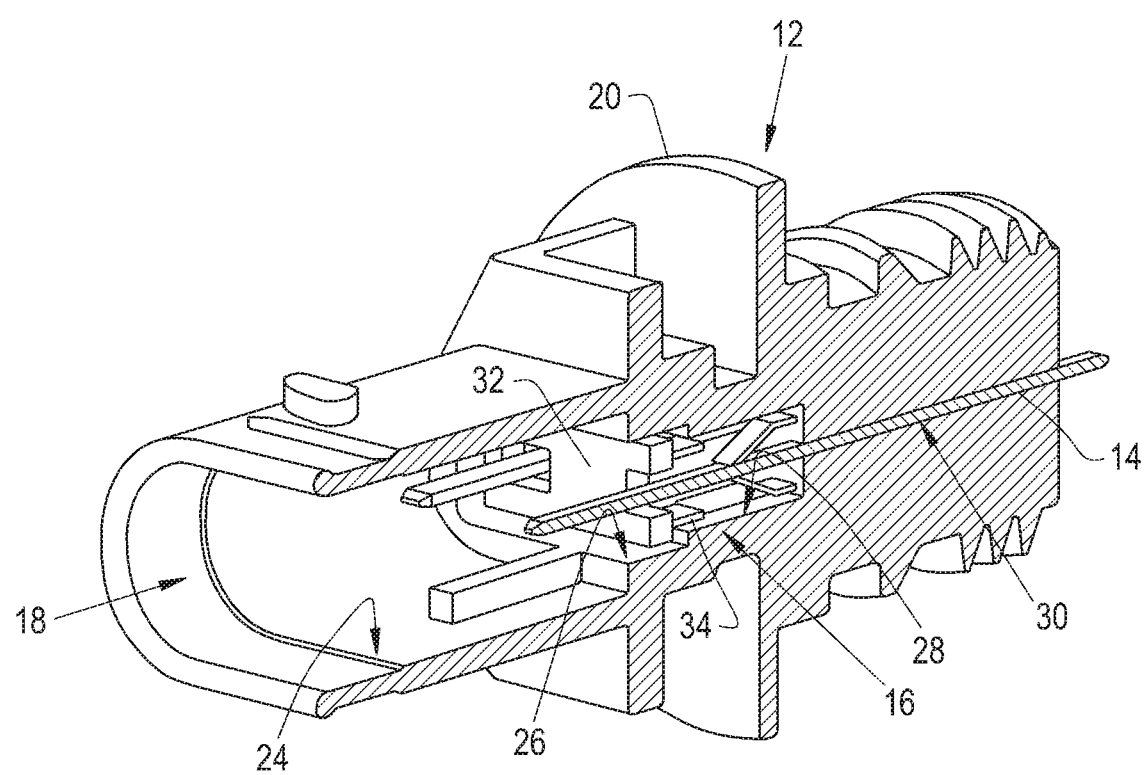
FIG. 2 is a cross-sectional perspective view of the sensor assembly, taken across line 2-2 in FIG. 1.
Figure 3:
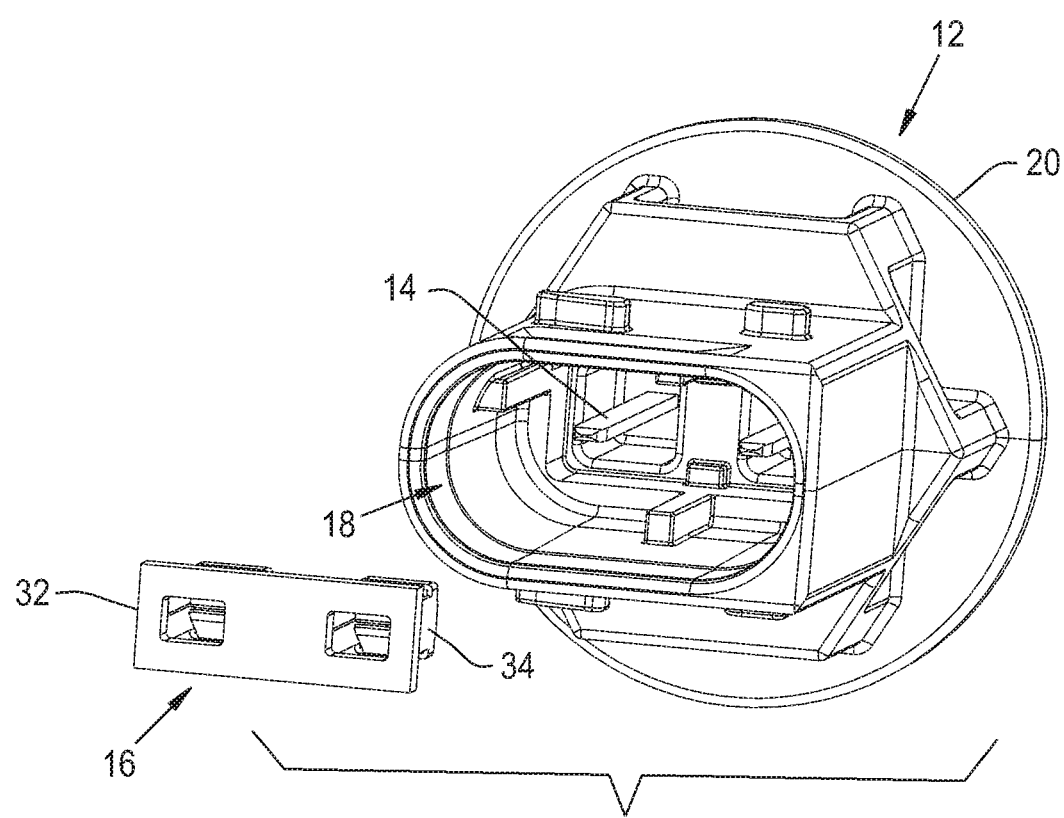
FIG. 3 is a front perspective and exploded view of the sensor assembly of FIG. 1.

The housing 12 may be connected to a housing of a fuel reservoir, a filter element, or other component of an engine system. The housing 12 may be in the form of a monolithic housing or a multipart housing. For example, the housing 12 may comprise a single component with a recess or bore 18 for receiving the pin(s) 14 and the board-mounting subassembly 16. Additionally, for example, the housing 12 may be in the form of a multipart housing 12 which includes a first connector 20 and a second connecter 22 that is sealably and/or removably connected to the first connector 20 (FIG. 1). The first connector 20 may include the recess 18 for receiving the pin(s) 14 and the board-mounting subassembly 16. The recess 18 may have one or more sections. For example, the recess 18 may have multiple sections 24, 26, 28, 30 of varying dimensions for receiving various portions of the board-mounting subassembly 16 and/or the pin(s) 14 (FIG. 2). The recess 18 may or may not extend throughout the first connector 20.

The one or more pins 14 may be located within and attached to the housing 12. The WIF sensor assembly 10 may include one, two, or more pins 14. Each pin 14 may be in the form of any desired electrode element. Each pin 14 may have any desired shape and size. For instance, each pin 14 may have a rectangular or circular cross-section.

The board-mounting subassembly 16 may include a circuit board 32, one or more terminals 34, one or more resistors 36, and various other electrical components. The circuit board 32, terminal(s) 34, and resistor(s) 36 may collectively define a subassembly which can be moved and attached to the housing 12 as one collective entity. Hence, the terminal(s) 34 and resistor(s) 36 may be coupled with the circuit board 32 to form the board-mounting subassembly 16. It should be appreciated that the board-mounting subassembly 16 may not include a resistor 36. It should also be appreciated that an epoxy may be applied onto the board-mounting subassembly 16. Additionally or alternatively, a sealing cap made of thermoplastic or a thermoset material may protect the circuit board 32 and/or board-mounting subassembly 16. Such a sealing cap may have a shape that corresponds to the circuit board 32 and/or board-mounting subassembly 16.

The board-mounting subassembly 16 may be positioned within the housing 12 and rigidly attached thereto by engaging the one or more terminals 34 with the one or more pins 14. The board-mounting subassembly 16 may be located in between and held in place by the connectors 20, 22 of the housing 12. Therein, the act of connecting the second connector 22 onto the first connector 20 may restrict a movement of the board-mounting subassembly 16 such that the board-mounting subassembly 16 is sandwiched in between the connectors 20, 22. In this regard, the board-mounting subassembly 16 is trapped between the connectors 20, 22 when they are joined together to make the resulting electro-mechanical connection therebetween. Advantageously, the board-mounting subassembly 16 may be easily installed, removed, or replaced as a result of joining the various components 32, 34, 36 together. Furthermore, the board-mounting subassembly 16 may eliminate the need for a separate circuit-board housing or mounting assembly for attaching a circuit board to corresponding pins.

The circuit board 32 may be fitted within the recess 18 of the housing 12. More particularly, the circuit board 32 may be fitted within one of the sections 26 of the recess 18 of the housing 12 (FIG. 2). The circuit board 32 may have one or more holes for receiving the pin(s) 14 therethrough. The circuit board 32 may be in the form of any desired circuit board.

Each terminal 34 can be surface mount soldered onto the circuit board 32. In other words, each terminal 34 may be a surface-mount terminal. Each terminal 34 may be located on the bottom side of the circuit board 32. Each terminal 34 may be in the form of any desired terminal. For example, each terminal 34 may be in the form of a box terminal. Each terminal 34 is engageable with a respective pin 14 such that the board-mounting subassembly 16 is disposed within the recess 18 of the housing 12. For instance, each terminal 34 can be slid or otherwise fitted onto a respective pin 14.

It should be appreciated that the shape of each terminal 34 may or may not correspond to the shape of a respective pin. Furthermore, each terminal 34 may be configured for receiving multiple different types of pins, for example square and round pins. The WIF sensor assembly 10 may include one, two, or more terminals 34 for engaging with a respective pin 14. It should be appreciated that the shape of the circuit board 32 and/or the individual or combined shape of the terminal(s) 34 may correspond to respective sections 26, 28 of the recess 18 of the housing 12 (FIG. 2).

Figure 4:
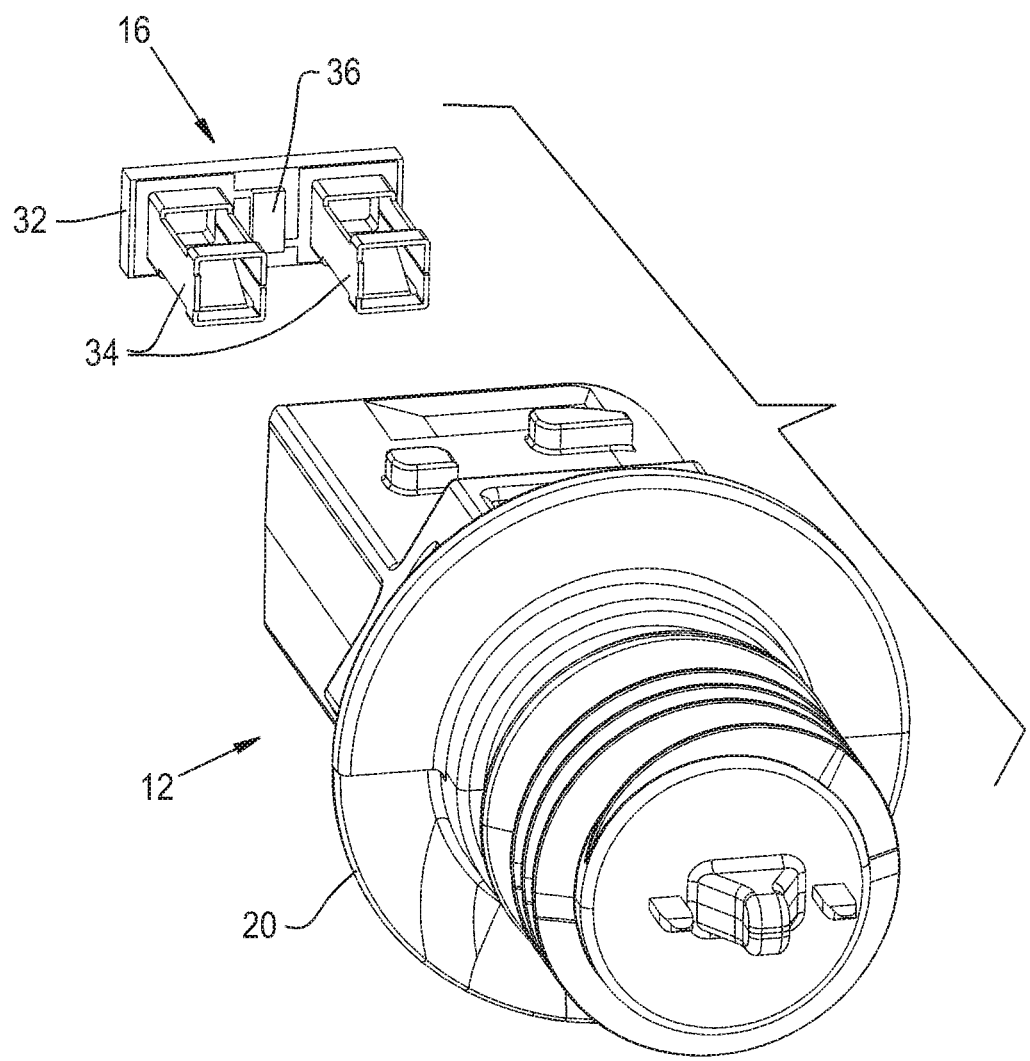
FIG. 4 is a rear perspective and exploded view of the sensor assembly of FIG. 1.

Each resistor 36 may be coupled to the circuit board 32 (FIG. 4). For example, each resistor 36 may be surface mount soldered onto the circuit board 32. Each resistor 36 may be connected to the bottom side of the circuit board 32. Each resistor 36 may be located in between the two terminals 34. Each resistor 36 may be connected in series with or parallel to the one or more terminals 34. Each resistor 36 may be in the form of any desired resistor.

An individual may conduct a method for assembling the WIF sensor assembly 10. As an initial step, the individual may provide the components of the WIF sensor assembly 10, as discussed above. Thereafter, the individual may form the board-mounting subassembly 16 by coupling each terminal 34 to the circuit board 32. The individual may also couple the resistors 36 to the circuit board 32. For example, the individual may surface mount solder the terminal(s) 34 and/or the resistor(s) 36 onto the circuit board 34. Thereafter, the individual may position the board-mounting subassembly 16 within the housing 12. For example, the individual may by engage each terminal 34 with a respective pin 14 such that the board-mounting subassembly 16 is disposed within the recess 18 of the housing 12. Thereafter, the individual may secure or lock the board-mounting subassembly 16 within the recess 18 of the housing 12 by connecting the second connector 22 to the first connector 20. Therein, the board-mounting subassembly 16 may be located in between and be immobilized by the connectors 20, 22.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of assembling a water-in-fuel sensor assembly, comprising:
  providing a housing comprising a recess, at least one pin located within the housing, a circuit board, and at least one terminal configured for engaging the at least one pin;
  forming a board-mounting subassembly by coupling the at least one terminal to the circuit board; and
  positioning the board-mounting subassembly within the housing by engaging the at least one terminal with the at least one pin such that the board-mounting subassembly is disposed within the recess of the housing, the water-in-fuel sensor assembly being configured for measuring an amount of water which may be present in a fuel, the circuit board and the at least one terminal at least in part forming the board-mounting subassembly which is a collective body which is readily installed and removed relative to the housing by way of a slidable connection between the at least one terminal and the at least one pin, the recess of the housing including a first section, a second section within which is disposed the circuit board, and a third section within which is disposed the at least one terminal, the second section being positioned between the first section and the third section such that the at least one pin extends sequentially through the third section and the second section and terminates in the first section.

2. The method of claim 1, wherein the board-mounting subassembly is rigidly attached to the housing by the at least one terminal engaging with the at least one pin.

3. The method of claim 1, wherein the housing is in the form of a multipart housing comprising a first connector and a second connector, wherein the first connector comprises the recess for receiving the board-mounting subassembly.

4. The method of claim 3, wherein the method further comprises a step of securing the board-mounting subassembly within the first connector by connecting the second connector to the first connector such that the board-mounting subassembly is located in between the first connector and the second connector and a movement of the board-mounting subassembly is restricted by the first connector and the second connector.

5. The method of claim 1, wherein the at least one terminal is surface mount soldered onto the circuit board.

6. The method of claim 1, wherein the at least one pin comprises at least two pins, wherein the at least one terminal comprises at least two terminals, wherein the step of forming the board-mounting subassembly comprises coupling the at least two terminals to the circuit board.

7. The method of claim 1, wherein the providing step further comprises providing at least one resistor, wherein the step of forming the board-mounting subassembly further comprises coupling the at least one resistor to the circuit board.

8. The method of claim 1, wherein the recess of the housing has a shape, wherein the circuit board has a shape which corresponds to the shape of the recess of the housing.

9. The method of claim 1, wherein the first section, the second section, and the third section each defines a space, the space of the second section communicating directly with the space of the first section and the space of the third section, each of the first section, the second section, and the third section including respectively a cross-sectional area which is perpendicular to a longitudinal extent of the at least one pin, the cross-sectional area of the second section being greater than the cross-sectional area of the third section and the cross-sectional area of the first section being greater than the cross-sectional area of the second section such that the board-mounting subassembly is configured for being readily installed and removed relative to the housing by way of passing through the first section.

10. A water-in-fuel sensor assembly, comprising:
a housing comprising a recess;
at least one pin located within the housing; and
a board-mounting subassembly located within the housing, the board-mounting subassembly comprising:
   a circuit board; and
   at least one terminal coupled to the circuit board, the at least one terminal being engaged with the at least one pin such that the board-mounting subassembly is disposed within the recess of the housing, the water-in-fuel sensor assembly being configured for measuring an amount of water which may be present in a fuel, the circuit board and the at least one terminal at least in part forming the board-mounting subassembly which is a collective body which is readily installed and removed relative to the housing by way of a slidable connection between the at least one terminal and the at least one pin, the recess of the housing including a first section, a second section within which is disposed the circuit board, and a third section within which is disposed the at least one terminal, the second section being positioned between the first section and the third section such that the at least one pin extends sequentially through the third section and the second section and terminates in the first section.

11. The water-in-fuel sensor assembly of claim 10, wherein the board-mounting subassembly is rigidly attached to the housing by the at least one terminal engaging with the at least one pin.

12. The water-in-fuel sensor assembly of claim 10, wherein the housing is in the form of a multipart housing comprising a first connector and a second connector removably connected to the first connector, wherein the first connector comprises the recess for receiving the board-mounting subassembly.

13. The water-in-fuel sensor assembly of claim 12, wherein the board-mounting subassembly is located in between the first connector and the second connector.

14. The water-in-fuel sensor assembly of claim 13, wherein a movement of the board-mounting subassembly is restricted by the first connector and the second connector.

15. The water-in-fuel sensor assembly of claim 10, wherein the at least one terminal is surface mount soldered onto the circuit board.

16. The water-in-fuel sensor assembly of claim 10, wherein the at least one pin comprises at least two pins.

17. The water-in-fuel sensor assembly of claim 16, wherein the at least one terminal comprises at least two terminals coupled to the circuit board.

18. The water-in-fuel sensor assembly of claim 10, wherein the board-mounting subassembly further comprises at least one resistor coupled to the circuit board.

19. The water-in-fuel sensor assembly of claim 10, wherein the recess of the housing has a shape, wherein the circuit board has a shape which corresponds to the shape of the recess of the housing.

20. The water-in-fuel sensor assembly of claim 10, wherein the first section, the second section, and the third section each defines a space, the space of the second section communicating directly with the space of the first section and the space of the third section, each of the first section, the second section, and the third section including respectively a cross-sectional area which is perpendicular to a longitudinal extent of the at least one pin, the cross-sectional area of the second section being greater than the cross-sectional area of the third section and the cross-sectional area of the first section being greater than the cross-sectional area of the second section such that the board-mounting subassembly is configured for being readily installed and removed relative to the housing by way of passing through the first section.

* * * * *